United States Patent
Noh et al.

(10) Patent No.: US 11,730,687 B2
(45) Date of Patent: Aug. 22, 2023

(54) EMULSION STRUCTURE FOR ENHANCING SKIN ABSORPTION AND METHOD OF PREPARING THE SAME

(71) Applicant: COSMAX, INC., Hwaseong-si (KR)

(72) Inventors: Min Joo Noh, Seongnam-si (KR); Jun Bae Lee, Yongin-si (KR); Myeong Sam Park, Seoul (KR)

(73) Assignee: COSMAX, INC., Gyeonggi-Do (KR)

( * ) Notice: Subject to any disclaimer, the term of this patent is extended or adjusted under 35 U.S.C. 154(b) by 542 days.

(21) Appl. No.: 16/731,326

(22) Filed: Dec. 31, 2019

(65) Prior Publication Data

US 2020/0206114 A1 Jul. 2, 2020

(30) Foreign Application Priority Data

Jan. 2, 2019 (KR) .................. 10-2019-0000183

(51) Int. Cl.
| | | |
|---|---|---|
| *A61K 8/42* | (2006.01) | |
| *A61K 8/06* | (2006.01) | |
| *A61K 8/60* | (2006.01) | |
| *A61K 9/00* | (2006.01) | |
| *A61K 9/107* | (2006.01) | |
| *A61K 47/18* | (2017.01) | |
| *A61K 47/44* | (2017.01) | |

(52) U.S. Cl.
CPC .................. *A61K 8/42* (2013.01); *A61K 8/06* (2013.01); *A61K 8/602* (2013.01); *A61K 9/0014* (2013.01); *A61K 9/107* (2013.01); *A61K 47/18* (2013.01); *A61K 47/44* (2013.01)

(58) Field of Classification Search
CPC ........ A61Q 19/00; A61K 47/18; A61K 47/44; A61K 8/06; A61K 8/066; A61K 8/345; A61K 8/42; A61K 8/602; A61K 8/68; A61K 8/86; A61K 9/0014; A61K 9/107
See application file for complete search history.

(56) References Cited

U.S. PATENT DOCUMENTS

| | | | |
|---|---|---|---|
| 9,687,423 B2 | 6/2017 | Lee et al. | |
| 9,744,243 B2 | 8/2017 | Lee et al. | |
| 9,949,900 B2 | 4/2018 | Lee et al. | |
| 2014/0220139 A1* | 8/2014 | Park | A61K 31/164 514/625 |
| 2019/0083368 A1 | 3/2019 | Hong et al. | |

FOREIGN PATENT DOCUMENTS

| | | |
|---|---|---|
| KR | 20060129890 A | 12/2006 |
| KR | 20140070430 A | 6/2014 |
| KR | 20150022434 A | 3/2015 |
| KR | 20150034451 A | 4/2015 |
| KR | 101819467 B1 | 1/2018 |

OTHER PUBLICATIONS

Pantelic, Natural-Origin Surfactants to Prospective Delivery Systems, Woodhead Publishing Series in Biomedicine, 2014, pp. 107-134 (Year: 2014).*
Fonseca-Santos, Int J Nanomedicine. 2016; 11: 4553-4562 (Year: 2016).*
Elias, et al., "Mammalian Epidermal Barrier Layer Lipids: Composition and Influence on Structure", J. Invest. Dermatol., vol. 69, No. 6, 1977, pp. 535-546.
Notice of Allowance dated Aug. 5, 2019, by the Korean Patent Office for Application No. 10-2019-0000183.
Office Action dated May 1, 2019, by the Korean Patent Office for Application No. 10-2019-0000183.

* cited by examiner

*Primary Examiner* — Jean P Cornet
(74) *Attorney, Agent, or Firm* — Panitch Schwarze Belisario & Nadel LLP

(57) ABSTRACT

Provided are an emulsion structure for enhancing skin absorption and a method of preparing the same. According to a composition of an aspect of the present disclosure, due to a hexagonal structure that can mimic intercellular lipid ingredients of skin, the composition has excellent formulation safety and piezoelectric properties capable of generating a microcurrent, and accordingly, the composition is able to enhance skin absorption of a physiologically active substance without damaging the skin barrier.

7 Claims, 1 Drawing Sheet

EMULSION STRUCTURE FOR ENHANCING SKIN ABSORPTION AND METHOD OF PREPARING THE SAME

CROSS-REFERENCE TO RELATED APPLICATION

This application claims the benefit of Korean Patent Application No. 10-2019-0000183, filed on Jan. 2, 2019, in the Korean Intellectual Property Office, the disclosure of which is incorporated herein in its entirety by reference.

BACKGROUND

1. Field

One or more embodiments relate to an emulsion structure for enhancing skin absorption, a cosmetic composition including the same, a composition for skin delivery, and a method of preparing the emulsion structure.

2. Description of Related Art

The skin barrier functions to prevent external harmful substances from being absorbed into the skin, and to keep moisture inside the skin from evaporating. Such functions of the skin barrier result from intercellular lipids in the stratum corneum. The intercellular lipids in the stratum corneum are known to be composed of, approximately, ceramides (50%), cholesterol (20% to 25%), free fatty acids (20% to 25%), cholesterol esters (10%), cholesterol sulfates (1% to 2%), and a small amount of phospholipids. In addition, these intercellular lipid ingredients are known to have a layered structure called a lamellar structure (refer to Non-Patent Document 1) and a structure in which orthorhombic packing and hexagonal packing are mixed. Here, an orthorhombic structure is a densely packed structure that serves to inhibit mass transfer through the intercellular lipids in the stratum corneum.

In this regard, to enhance skin absorption of a physiologically active substance, a chemical skin penetration enhancer may be used. However, a commonly used chemical skin penetration enhancer, such as alcohol, menthol, urea, or the like, enhances skin absorption of a potent ingredient by destroying the intercellular lipids in the stratum corneum or modifying the structure of lipids, and consequently, skin barrier damage and various stimulations and irritation are caused by the modification of the intercellular lipid ingredients.

Therefore, there is a need for the development of a cosmetic that can enhance the skin absorption of a physiologically active substance without damaging the skin barrier, by mimicking the skin structure without using a skin penetration enhancer.

PRIOR ART DOCUMENTS

Non-Patent Document (Non-Patent Document 1) J. Invest. Dermatol. 69: 535-546, 1977.

SUMMARY

One or more embodiments include, to solve the problems described above, a cosmetic composition of an emulsion formulation having a hexagonal crystal structure.

One or more embodiments include a composition of an emulsion formulation having a hexagonal crystal structure for delivering a physiologically active substance to skin.

Additional aspects will be set forth in part in the description which follows and, in part, will be apparent from the description, or may be learned by practice of the presented embodiments of the disclosure.

According to one or more embodiments, there is provided a cosmetic composition of an emulsion formulation having a hexagonal crystal structure.

According to one or more embodiments, there is provided a composition of an emulsion formulation having a hexagonal crystal structure for delivering a physiologically active substance to skin.

In one embodiment, the cosmetic composition or the composition may include: an oil phase including ceramide or a derivative thereof and a surfactant; and a liquid phase including polyol.

The term "hexagonal system" as used herein is used interchangeably with "hexagonal structure", "hexagonal type", or "hexagonal crystal system", and may refer to a crystal structure in which substances, such as surfactants, in emulsion are arranged. In addition, in the hexagonal system, a sharp single peak derived from the hexagonal system on a cross section in a wide angle region may be observed. For example, a peak may be observed at 1.52 Å-in wide angle X-ray scattering analysis. Since a hexagonal structure typically has a loose or open crystal structure, molecules have increased movement and a polarization phenomenon easily occurs, and accordingly, the hexagonal structure may have strong piezoelectric properties capable of generating a microcurrent and an effect of enhancing skin absorption of a physiologically active substance. Thus, the cosmetic composition or the composition may enhance skin absorption (transdermal delivery) of ceramide or a derivative thereof and a physiologically active substance.

The term "ceramide" is used interchangeably with N-acylsphingosine, and may refer to all compounds consisting of sphingosine and fatty acid. Examples of ceramide include natural ceramide, synthetic ceramide, or a derivative of natural ceramide or synthetic ceramide. Ceramide may include at least one selected from ceramide EOP, ceramide NG, ceramide NS, ceramide NP, ceramide AS, and ceramide AP. The derivative of ceramide may include a known derivative having properties similar to ceramide. An amount of ceramide or the derivative thereof may be in a range of about 0.01 weight % to about 3 weight %, about 0.01 weight % to about 2 weight %, about 0.05 weight % to about 2 weight %, about 0.1 weight % to about 1 weight %, or about 0.2 weight % to about 0.8 weight %, based on the total amount of the cosmetic composition or the composition. When the amount of ceramide or the derivative thereof is less than about 0.01 weight %, the effect of enhancing the skin absorption may not be sufficiently exhibited, and when the amount of ceramide or the derivative thereof is greater than about 3 weight %, the cosmetic composition or the composition may be subjected to gelation in an aqueous phase, or may be precipitated due to difficult dissolution.

In one embodiment, the surfactant may include a non-ionic surfactant. In addition, the non-ionic surfactant may include a glucoside-based surfactant. In more detail, the glucoside-based surfactant may include at least one selected from cetearyl glucoside, decyl glucoside, coco-glucoside, behenyl alcohol, arachidyl alcohol, arachidyl glucoside, and $C_{10}$-$C_{20}$ alkyl glucoside. An amount of the surfactant may be in a range of about 0.1 weight % to about 5 weight %, about 0.5 weight % to about 5 weight %, about 0.5 weight % to about 4 weight %, about 0.8 weight % to about 4 weight %, or about 1 weight % to about 3 weight %, based on the total amount of the cosmetic composition or the composition.

In one embodiment, the oil phase may further include higher fatty alcohol or oil.

The higher fatty alcohol may include batyl alcohol, behenyl alcohol, cetostearyl alcohol, cetyl alcohol, or stearyl alcohol.

The oil may include ester oil, hydrocarbon-based oil, silicone oil, vegetable oil, or a mixture thereof. The ester oil may include $C_{12}$-$C_{15}$ alkyl octanoate, myristyl lactate, cetyl octanoate, isopropyl myristate, octyldodecyl myristate, hexyl laurate, di($C_{12}$-$C_{13}$) alkyl malate, myristyl lactate, octyldodecyl stearoyl stearate, diisostearyl malate, pentaerythrityl tetraisostearate, or diglyceryl triisostearate. The hydrocarbon-based oil of the present disclosure may include hydrogenated oil, hydrogenated PEG-60 castor oil, hydrogenated polyisobutene, or hydrogenated polydecene. The silicone oil may include dimethicone, phenyl trimethicone, dimethicone/trimethylsiloxysilicate, diphenyl dimethicone, or triphenyl methicone. The vegetable oil may include shea butter oil, mango butter oil, cocoa seed butter oil, macadamia nut oil, olive oil, meadow foam seed oil, purified grape seed oil, peach kernel oil, or sunflower seed oil.

An amount of the higher fatty alcohol or the oil may be in a range of about 0.1 weight % to about 10 weight %, about 0.5 weight % to about 10 weight %, about 0.5 weight % to about 8 weight %, about 0.8 weight % to about 6 weight %, or about 0.8 weight % to about 6 weight %, based on the total amount of the cosmetic composition or the composition.

The liquid phase may include polyol, water, and/or other ingredients.

The terms "polyol" and "polyhydric alcohol" are used interchangeably, and may refer to an aliphatic compound having two or more hydroxyl groups (—OH). The polyol may include glycerol, glycol, or a combination thereof. The glycerol may include glycerin, diglycerin, polyglycerin, glyceritol, glycyl alcohol, or a combination of two or more thereof. The glycerin may be used interchangeably with other commonly used names, such as glycerin, propane-1, 2,3-triol, 1,2,3-propanetriol, trihydroxy propane, or the like. The glycol may include propylene glycol, dipropylene glycol, butylene glycol, diethylene glycol, triethylene glycol, hexylene glycol, pentylene glycol, polyethylene glycol, or a combination of two or more thereof. An amount of the polyol may be in a range of about 1 weight % to about 20 weight %, about 2 weight % to about 20 weight %, about 4 weight % to about 20 weight %, about 4 weight % to about 16 weight %, or about 6 weight %, to about 14 weight %, based on the total amount of the cosmetic composition or the composition. When the amount of the polyol in the liquid phase is less than about 1%, the polyol may have a problem with microbial inhibitory effects, and when the amount of the polyol in the liquid phase is greater than about 30%, the polyol may have a problem causes sticky usage feeling.

The cosmetic composition or the composition may have piezoelectric properties. Without being limited to a specific theory, since the hexagonal structure has an open crystal structure, molecules have increased movement which causes the polarization phenomenon, resulting in strong piezoelectric properties. Therefore, the cosmetic composition or the composition may be a piezoelectric composition or a piezoelectric cosmetic.

The term "piezoelectric composition" or "piezoelectric cosmetic" as used herein may refer to a substance capable of generating a microcurrent upon the application of pressure, and due to the generated microcurrent, the delivery (transdermal delivery) of the physiologically active substance including ceramide or the like to the skin may be enhanced.

A piezoelectric constant of the cosmetic composition or the composition may be, for example, in a range of about 60 pC to about 120 pC, about 70 pC to about 110 pC, or about 80 pC to about 100 pC.

In one embodiment, the cosmetic composition or the composition may further include the physiologically active substance in the oil phase or the liquid phase. The physiologically active substance is not particularly limited as long as it is soluble in the cosmetic composition or the composition. The term "skin" is mentioned throughout the present specification, and in detail, the skin may include a substance that is delivered through the skin (also, referred to as transdermal delivery) and may exhibit a systemic effect.

The physiologically active substance described in the present disclosure is not limited to a low-molecular drug, and may also include a biological compound, such as a protein, a peptide, an enzyme, DNA, RNA, siRNA, an antibody or a fragment thereof, a vitamin, a mineral, or a combination thereof.

To enhance the effect or distribution profile of the physiologically active substance, other compounds or excipients may be added to the cosmetic composition or the composition.

The physiologically active substance as used herein may be generally selected from: a whitening agent, an anti-wrinkle agent, a sunscreen agent, an atopy enhancer or therapeutic agent, an acne enhancer or therapeutic agent, an antioxidant, an analgesic, an anti-inflammatory agent, an anti-infective agent, a wound- or scar-healing agent, an antipyrotic, a nutritional supplement, a mineral, and a vitamin.

The cosmetic composition may have an O/W (water-in-oil) emulsion formulation. However, the formulation of the cosmetic composition is not particularly limited, and depending on the formulation to be prepared, the formulation may include blending ingredients of the cosmetic composition used in the art. The cosmetic composition of the present disclosure may be, for example, formulated as a liquid product, a lotion, an essence, a sun lotion, a sun cream, a makeup base, a foundation, a BB cream, a stick-like product, or a balm-type product. However, the embodiments are not limited thereto. In addition, according to the formulation to be prepared, oil, water, a surfactant, a moisturizer, lower alcohol, a thickener, a chelating agent, a preservative, a fragrance, or the like may be selected and added for blending. In addition, the cosmetic composition may further include a sunscreen agent, a light-scattering agent, or the like, and the formulation and the additives are not limited to the descriptions provided above. In addition, these ingredients may be introduced in amounts generally used in the art of dermatology.

The cosmetic composition may further include additional ingredients commonly used in cosmetics, such as a thickener, a dispersant, a flavoring, a filler, a preservative, a neutralizing agent, a sweetener, a vitamin, a free-radical scavenger, a chelating agent, a functional substance, and a mixture thereof.

Those skilled in the art may select any additional ingredient and/or an amount thereof such that the advantageous properties of the cosmetic composition or the composition of the present disclosure are not adversely affected or substantially influenced by the expected addition.

In addition, the cosmetic composition or the composition may be an external preparation for the skin. The external preparation for the skin may be a composition for transdermal delivery of a drug (e.g., the physiologically active substance).

In the present specification, the external preparation for the skin may be cream, gel, skin emulsifier, skin suspension, transdermal patch, drug-containing bandage, lotion, or a combination thereof. The external preparation for the skin may be prepared by appropriately blending, as necessary, ingredients usually used for external preparation for skins, such as aqueous ingredients, oily ingredients, powder ingredients, alcohols, humectants, thickeners, ultraviolet absorbers, whitening agents, preservatives, antioxidants, surfactants, flavors, colorants, various skin nutrients, or a combination thereof.

The external preparation for the skin may be prepared by appropriately blending chelating agents, such as edate disodium, edate trisodium, sodium citrate, sodium polyphosphate, sodium metaphosphate, gluconic acid, or the like; drugs, such as caffeine, tannin, verapamil, glycyrrhiza extracts, glabridin, hot-water extracts of a fruit of calines, various herbs, tocopherol acetate, glytilinic acid, tranexamic acid and a derivative or salt thereof, or the like; and sugars, such as, vitamin C, ascorbyl magnesium phosphate, ascorbyl glucoside, albutin, kojic acid, glucose, fructose, treshalose, or the like.

According to one or more embodiments, there is provided a method of preparing a composition of an emulsion formulation having a hexagonal crystal structure.

The method may include: preparing an oil phase by mixing a surfactant with ceramide or a derivative thereof, and dissolving the mixture at a raised temperature in a range of about 80° C. to about 90° C.; preparing a liquid phase by mixing water with a polyol ingredient, and dissolving the mixture at a raised temperature; and preparing a mixed solution of the oil phase and the liquid phase by adding and stirring the oil phase to the liquid phase at a temperature in a range of about 70° C. to about 80° C.

In addition, the method may further include: mixing and stirring the mixed solution with a thickener and/or a preservative; and/or removing bubbles after cooling the reactants of the stirring at a temperature of at least 40° C.

BRIEF DESCRIPTION OF THE DRAWINGS

The above and other aspects, features, and advantages of certain embodiments of the disclosure will be more apparent from the following description taken in conjunction with the accompanying drawings, in which.

DETAILED DESCRIPTION

Figure 1:
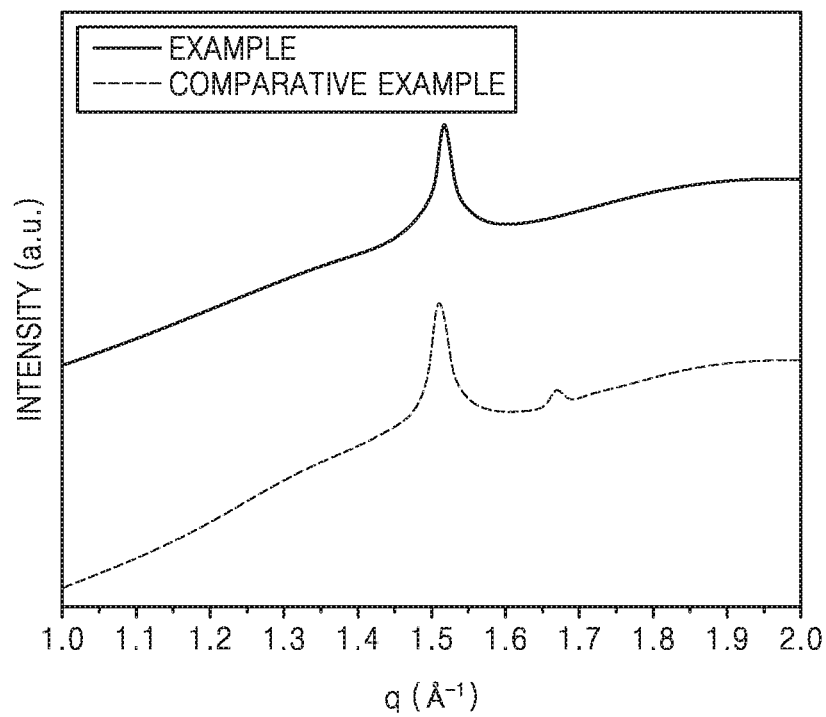
FIG. 1 is a wide-angle X-ray scattering graph of a cosmetic composition according to an embodiment.

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects of the present description. As used herein, the term "and/or" includes any and all combinations of one or more of the associated listed items. Expressions such as "at least one of," when preceding a list of elements, modify the entire list of elements and do not modify the individual elements of the list.

Example: Preparation of Cosmetic Composition Having Hexagonal Structure

Cosmetic compositions having compositions of Table 1 below (unit: weight %) were prepared in Example and Comparative Example. In the cosmetic compositions of Comparative Example, surfactants based on cetyl palmiate, sorbitan olivate, sorbitan palmitate, or the like were used, and in the cosmetic compositions of Example, surfactants based on alkyl glucoside were used.

In detail, according to each ingredient and content shown in Table 1, each raw material was weighed in a beaker, and then, Phase A (i.e., oil phase) was dissolved at a raised temperature in a range of 80° C. to about 90° C., and the resulting phase was slowly added to Phase B (i.e., liquid phase) at room temperature. Here, the mixture of Phase A and Phase B was constantly stirred, and then, Part C (i.e., a thickener) was added thereto and stirred. The resulting mixture was cooled to a temperature of 30° C., and Part D (i.e., a preservative) was added thereto. Afterwards, bubbles were removed from the cooled mixture, thereby preparing each cosmetic composition.

TABLE 1

| | | Content (weight %) | |
| | | Comparative | |
| | Ingredients | Example | Example |
| --- | --- | --- | --- |
| A | Cetearyl alcohol | 1.0 | 1.0 |
| | Cetyl palmiate | 0.8 | 0 |
| | Sorbitan olivate | 0.6 | 0 |
| | Sorbitan palmiate | 0.6 | 0 |
| | $C_{12}$-$C_{20}$ alkyl glucoside | 0 | 2.0 |
| | Ceramide | 0.5 | 0.5 |
| | Caprlic/Capric triglyceride | 3.5 | 3.5 |
| B | Purified water | Suitable amount | Suitable amount |
| | Glycerin | 10 | 10 |
| C | Cabomer | Suitable amount | Suitable amount |
| D | Preservative | Suitable amount | Suitable amount |

Experimental Example 1: Evaluation of Skin Safety

The skin safety evaluation was performed with respect to the cosmetic compositions of Example and Comparative Example.

In detail, for 20 adult men and women having no skin disease, the degree of irritation of the formulations prepared in Example e and Comparative Example was evaluated as follows. 20 µl of a sample was applied to the forearms of the testers, and then, the test site was sealed and patched for 24 hours. In 30 minutes and 24 hours after removal of the patch, the skin response was examined based on the terminology set forth in the CTFA guidelines. The skin irritation index (PII) scores of the testers obtained by the criteria were averaged and evaluated as 'hypoallergenic' for the average value of less than 1, 'light irritation' for the average value of less than 2, 'moderate irritation' for the average value of less than 3.5, and 'strong irritation' for the average value of 3.5 or greater.

TABLE 2

| Experiment item | Comparative Example | Example |
| --- | --- | --- |
| Primary Irritation Index (P.I.I) | No irritation | No irritation |

As shown in Table 2, it was confirmed that the compositions of Example and Comparative Example were products causing no irritation, and thus, may be used safely.

Experimental Example 2: Analysis of Crystal Structure of Emulsion Formulation

To analyze the emulsion structure of the compositions of Example and Comparative Example, the wide angle X-ray scattering (WAXS) analysis (available by BL4C SAXS, Pohang Accelerator Laboratory) was performed, and the results are shown in FIG. 1.

FIG. 1 is a wide angle X-ray scattering graph of a cosmetic composition according to an embodiment.

As shown in FIG. 1, in the case of the comparative Example of the Comparative Example, peaks were observed at 1.51 $Å^{-1}$ and 1.67 $Å^{-1}$. When substituting the Bragg equation (d=2π/q) to obtain d-spacing which represents the size of a structure, the obtained values were 0.416 nm and 0.376 nm, which refers to a orthorhombic packing structure which is a densely packed structure.

However, in the case of the composition of Example, a peak was observed at 1.52 $Å^{-1}$. When substituting the Bragg equation (d=2π/q) to obtain d-spacing which represents the size of a structure, the obtained value was 0.414 nm, which refers to a hexagonal packing structure which is a relatively loosely packed structure.

Therefore, it was confirmed that, depending on the types of the surfactant, the packing of the molecules at the interface varied, resulting in different structures. In addition, it was also confirmed that a cosmetic composition of an emulsion formulation having a hexagonal crystal structure was prepared herein.

Experimental Example 4: Confirmation of Skin Absorption Effect

To evaluate skin absorption effect of ceramide under in vitro conditions with respect to the compositions of Example and Comparative Example, experiments using Franz cells were performed.

In detail, the artificial membrane (Strat-M) manufactured by Merck Company was placed inside an open-type glass laboratory apparatus, and an appropriate amount of each of the compositions of Example and Comparative Example was applied thereon and then sufficiently absorbed. The acceptor portion was filled with 13 mL of 50:50 PBS/EtOH (v/v), and the penetration experiment was performed at a temperature of 32° C. After 1, 2, 4, and 8 hours, the receptor portion which penetrated the artificial membrane using the solvent (50:50 PBS/EtOH (v/v)) was extracted, and the concentration of ceramide was measured by HPLC analysis. The conditions for HPLC analysis are shown in Table 3.

TABLE 3

| Column | $C_{15}$ (250 × 4.6 mm, 5 μm, 300 A, Jupiter) |
| --- | --- |
| Detector | Reversed phase high-pressure liquid chromatography (UltiMate 3000, Dionex) |
| Flow rate | 1.0 ml/min |
| Absorbance | 325 nm |
| Mobile phase | 90% methanol, isocratic elution |

Figure 2:
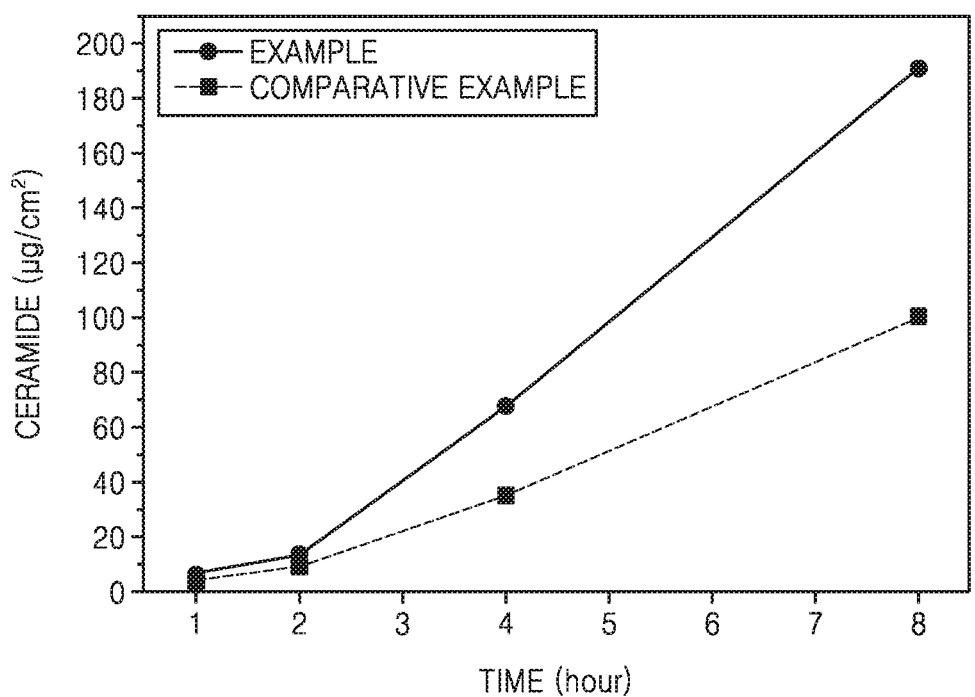
FIG. 2 is a graph showing an in vitro skin absorption effect of a cosmetic composition according to an embodiment.

Then, the HPLC data results are shown in FIG. 2.

FIG. 2 is a graph showing in vitro skin absorption effect of a cosmetic composition according to an embodiment.

AS shown in FIG. 2, the composition of Example having a hexagonal packing structure which is a relatively loose structure showed excellent skin absorption under in vitro conditions, compared to the compositions of Comparative Example having an orthorhombic packing structure which is a dense structure.

Experimental Example 5: Piezoelectricity Test

To evaluate piezoelectric properties of the compositions of Example and Comparative Example, the liquid-phase piezoelectric measuring device (refer to KR10-1793902) was used to measure piezoelectric properties.

In detail, 2 ml of each sample of Comparative Example and Example was placed between electrodes of the liquid-phase piezoelectric measuring device, a motor stage was moved and sampled, and then, the force was repeatedly applied to the samples at a rotation angle of 10°. Afterwards, electric charges generated in the samples were measured to measure piezoelectric properties, and the results are shown in Table 4.

TABLE 4

| Experiment item | Comparative Example | Example |
| --- | --- | --- |
| Piezoelectric property (pC) | 51.62 | 91.18 |

As a result, as shown in Table 4, it was confirmed that the composition of Example having a hexagonal packing structure had high piezoelectricity. In other words, it was confirmed that, due to the relatively loose structure, molecules had increased movement and the polarization phenomenon easily occurred, resulting in strong piezoelectric properties.

Regarding the composition according to an aspect of the present disclosure, the composition has a hexagonal structure that can mimic the intercellular lipid ingredients of the skin, and accordingly, the formulation of the composition is safe and the composition may have piezoelectric properties that can generate a microcurrent. Thus, the composition may have an effect that can enhance the skin absorption of the physiologically active substance without damaging the skin barrier.

It should be understood that embodiments described herein should be considered in a descriptive sense only and not for purposes of limitation. Descriptions of features or aspects within each embodiment should typically be considered as available for other similar features or aspects in other embodiments. While one or more embodiments have been described with reference to the figures, it will be understood by those of ordinary skill in the art that various changes in form and details may be made therein without departing from the spirit and scope of the disclosure as defined by the following claims.

What is claimed is:

1. A cosmetic composition for enhancing skin absorption formulated as an emulsion having a hexagonal crystal structure, comprising:
    an oil phase comprising ceramides or derivatives thereof and a glucoside-based surfactant; and
    a liquid phase comprising polyols,
    wherein the glucoside-based surfactant is $C_{12}$-$C_{20}$ alkyl glucoside,
    wherein an amount of the surfactant is in a range of 1 weight % to 3 weight % based on the total amount of the cosmetic composition, and
    wherein an amount of the ceramides or the derivatives thereof is in a range of 0.1 weight % to 1 weight % based on the total amount of the cosmetic composition.

2. The cosmetic composition of claim 1, wherein the derivatives of the ceramides comprise at least one selected from ceramide EOP, ceramide NG, ceramide NS, ceramide NP, ceramide AS, and ceramide AP.

3. The cosmetic composition of claim 1, wherein the oil phase or the liquid phase further comprises a physiologically active substance.

4. The cosmetic composition of claim 1, wherein the cosmetic composition has a piezoelectric constant in a range of 60 pC to 120 pC.

5. The cosmetic composition of claim 1, wherein the cosmetic composition is a piezoelectric cosmetic.

6. The cosmetic composition of claim 1, wherein the cosmetic composition enhances skin absorption of the ceramides or derivatives thereof.

7. A composition for delivering a physiologically active substance to skin, the composition being formulated as an emulsion having a hexagonal crystal structure, and comprising:
    an oil phase comprising ceramides or derivatives thereof and a glucoside-based surfactant;
    a liquid phase comprising polyols; and
    the physiologically active substance at least one selective from the group consisting of whitening agent, a sunscreen agent, an atopy enhancer or therapeutic agent, an antioxidant, an analgesic, an anti-inflammatory agent, an anti-infective agent, a wound- or scar-healing agent, an antipyrotic, a nutritional supplement, a mineral, and a vitamin;
    wherein the glucoside-based surfactant is $C_{12}$-$C_{20}$ alkyl glucoside,
    wherein an amount of the surfactant is in a range of 1 weight % to 3 weight% based on the total amount of the cosmetic composition, and
    wherein an amount of the ceramides or the derivatives thereof is in a range of 0.1 weight % to 1 weight % based on the total amount of the cosmetic composition.

* * * * *